United States Patent
Brannan

(10) Patent No.: US 10,799,290 B2
(45) Date of Patent: Oct. 13, 2020

(54) MICROWAVE TISSUE DISSECTION AND COAGULATION

(71) Applicant: Covidien LP, Mansfield, MA (US)

(72) Inventor: Joseph D. Brannan, Lyons, CO (US)

(73) Assignee: COVIDIEN LP, Mansfield, MA (US)

( * ) Notice: Subject to any disclaimer, the term of this patent is extended or adjusted under 35 U.S.C. 154(b) by 194 days.

(21) Appl. No.: 16/159,043

(22) Filed: Oct. 12, 2018

(65) Prior Publication Data

US 2019/0046266 A1 Feb. 14, 2019

Related U.S. Application Data

(60) Division of application No. 14/922,811, filed on Oct. 26, 2015, now Pat. No. 10,098,697, which is a
(Continued)

(51) Int. Cl.
*A61B 18/18* (2006.01)
*A61B 17/3211* (2006.01)
*A61B 18/00* (2006.01)

(52) U.S. Cl.
CPC ...... *A61B 18/1815* (2013.01); *A61B 17/3211* (2013.01); *A61B 2017/32113* (2013.01);
(Continued)

(58) Field of Classification Search
CPC ............ A61B 18/1815; A61B 17/3211; A61B 2018/00023; A61B 2018/00035;
(Continued)

(56) References Cited

U.S. PATENT DOCUMENTS 3,461,261 A 8/1969 Lewis
4,114,623 A 9/1978 Meinke et al.
(Continued)

FOREIGN PATENT DOCUMENTS

CN 1103807 A 6/1995
CN 101926046 A 12/2010
(Continued)

OTHER PUBLICATIONS

International Search Report PCT/US01/11340 dated Aug. 16, 2001.
(Continued)

*Primary Examiner* — Michael F Peffley
*Assistant Examiner* — Yasamin Ekrami

(57) ABSTRACT

A surgical instrument is configured to concurrently dissect and coagulate tissue. The surgical instrument includes a handle and a shaft extending distally from the handle. The shaft includes an outer hypotube, a lumen coaxially-disposed within the hypotube and extending beyond a distal end thereof, a coaxial feedline coaxially-disposed within the lumen, and having an inner conductor and an outer conductor disposed coaxially about the inner conductor, and a coolant tube coaxially-disposed between the lumen and the coaxial feedline to form an inflow conduit and an outflow conduit. The instrument further includes a dissecting head assembly coupled to a distal end of the shaft. The dissecting head assembly includes a dielectric core having a substantially planar radiating surface and at least one non-radiating surface, a reflective coating disposed on the at least one non-radiating surface of the dielectric core, and a blade extending from the radiating surface.

11 Claims, 4 Drawing Sheets

Related U.S. Application Data continuation of application No. 13/083,256, filed on Apr. 8, 2011, now Pat. No. 9,198,724.

(52) U.S. Cl.
CPC ........... *A61B 2018/00023* (2013.01); *A61B 2018/00035* (2013.01); *A61B 2018/00142* (2013.01); *A61B 2018/00607* (2013.01)

(58) Field of Classification Search
CPC ........... A61B 2017/32113; A61B 2018/00142; A61B 2018/00607
See application file for complete search history.

(56) References Cited

U.S. PATENT DOCUMENTS

| | | | |
|---|---|---|---|
| 4,273,127 A * | 6/1981 | Auth | A61B 17/3211 606/3 |
| 4,446,874 A | 5/1984 | Vaguine | |
| D278,306 S | 4/1985 | McIntosh | |
| 4,517,976 A | 5/1985 | Murakoshi et al. | |
| 4,534,347 A * | 8/1985 | Taylor | A61B 17/3211 606/33 |
| D295,893 S | 5/1988 | Sharkany et al. | |
| D295,894 S | 5/1988 | Sharkany et al. | |
| 4,850,353 A | 7/1989 | Stasz et al. | |
| 4,862,890 A | 9/1989 | Stasz et al. | |
| D354,218 S | 1/1995 | Van de Peer | |
| 5,456,684 A | 10/1995 | Schmidt et al. | |
| 5,647,871 A | 7/1997 | Levine et al. | |
| 5,702,387 A | 12/1997 | Arts et al. | |
| 5,766,166 A | 6/1998 | Hooven | |
| 5,836,897 A | 11/1998 | Sakurai et al. | |
| 5,906,487 A | 5/1999 | Carr | |
| D424,693 S | 5/2000 | Pruter | |
| D424,694 S | 5/2000 | Tetzlaff et al. | |
| D425,201 S | 5/2000 | Tetzlaff et al. | |
| RE36,795 E | 7/2000 | Rydell | |
| 6,200,313 B1 * | 3/2001 | Abe | A61B 18/1477 606/34 |
| 6,206,876 B1 | 3/2001 | Levine et al. | |
| D449,886 S | 10/2001 | Tetzlaff et al. | |
| 6,312,452 B1 | 11/2001 | Dobak, III et al. | |
| D457,958 S | 5/2002 | Dycus et al. | |
| D457,959 S | 5/2002 | Tetzlaff et al. | |
| 6,409,725 B1 | 6/2002 | Khandkar et al. | |
| 6,413,255 B1 | 7/2002 | Stern | |
| 6,419,675 B1 | 7/2002 | Gallo, Sr. | |
| 6,511,479 B2 | 1/2003 | Gentelia et al. | |
| 6,589,239 B2 | 7/2003 | Khandkar et al. | |
| 6,616,661 B2 | 9/2003 | Wellman et al. | |
| D487,039 S | 2/2004 | Webster et al. | |
| 6,692,489 B1 | 2/2004 | Heim et al. | |
| D496,997 S | 10/2004 | Dycus et al. | |
| D499,181 S | 11/2004 | Dycus et al. | |
| 6,936,024 B1 | 8/2005 | Houser | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| 7,175,621 B2 | 2/2007 | Heim et al. | |
| D541,418 S | 4/2007 | Schechter et al. | |
| D541,938 S | 5/2007 | Kerr et al. | |
| 7,255,697 B2 | 8/2007 | Dycus et al. | |
| 7,270,656 B2 | 9/2007 | Gowda et al. | |
| D564,662 S | 3/2008 | Moses et al. | |
| D576,932 S | 9/2008 | Strehler | |
| 7,419,488 B2 | 9/2008 | Ciarrocca et al. | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| D634,010 S | 3/2011 | DeCarlo | |
| 8,586,897 B2 | 11/2013 | Cronin | |
| 9,198,724 B2 | 12/2015 | Brannan | |
| 2005/0096645 A1 | 5/2005 | Wellman et al. | |
| 2005/0096646 A1 | 5/2005 | Wellman et al. | |
| 2005/0234442 A1 | 10/2005 | Spears | |
| 2006/0167452 A1 | 7/2006 | Moses et al. | |
| 2006/0259024 A1 | 11/2006 | Turovskiy et al. | |
| 2006/0264923 A1 | 11/2006 | Prakash et al. | |
| 2007/0016180 A1 | 1/2007 | Lee et al. | |
| 2007/0203551 A1 | 8/2007 | Cronin et al. | |
| 2007/0233057 A1 | 10/2007 | Konishi | |
| 2007/0260242 A1 | 11/2007 | Dycus et al. | |
| 2008/0114352 A1 | 5/2008 | Long et al. | |
| 2008/0294162 A1 | 11/2008 | Rossetto et al. | |
| 2010/0137856 A1 * | 6/2010 | Burdio Pinilla | A61B 18/148 606/33 |
| 2010/0168741 A1 | 7/2010 | Sanai et al. | |
| 2010/0286687 A1 | 11/2010 | Feldberg et al. | |
| 2010/0305559 A1 | 12/2010 | Brannan et al. | |
| 2011/0040300 A1 | 2/2011 | Brannan | |
| 2011/0066144 A1 | 3/2011 | Bonn et al. | |
| 2011/0077633 A1 | 3/2011 | Bonn et al. | |

FOREIGN PATENT DOCUMENTS

| | | |
|---|---|---|
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 3/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 0150253 A2 | 8/1985 |
| EP | 0246350 A1 | 11/1987 |
| EP | 0521264 A2 | 1/1993 |
| EP | 0556705 A1 | 8/1993 |
| EP | 0558429 A1 | 9/1993 |
| EP | 0648515 A1 | 4/1995 |
| EP | 0836868 A2 | 4/1998 |
| EP | 0882955 A1 | 12/1998 |
| EP | 1159926 A2 | 3/2003 |
| EP | 1532932 A1 | 5/2005 |
| EP | 1535581 A2 | 6/2005 |
| EP | 1609430 A1 | 12/2005 |

(56) References Cited

FOREIGN PATENT DOCUMENTS

| | | | |
|---|---|---|---|
| EP | 2233098 A1 | 9/2010 |
| EP | 2255742 A1 | 12/2010 |
| EP | 2371318 A1 | 10/2011 |
| FR | 179 607 | 11/1906 |
| FR | 1275415 A | 11/1961 |
| FR | 1347865 A | 1/1964 |
| FR | 2 235 669 A1 | 1/1975 |
| FR | 2 276 027 A1 | 1/1976 |
| FR | 2313708 A1 | 12/1976 |
| FR | 2502935 A1 | 10/1982 |
| FR | 2517953 A1 | 6/1983 |
| FR | 2573301 A1 | 5/1986 |
| FR | 2 862 813 A1 | 5/2005 |
| FR | 2 864 439 A1 | 7/2005 |
| GB | 2415630 A | 1/2006 |
| JP | 55106 | 1/1993 |
| JP | 0540112 | 2/1993 |
| JP | H0540112 A | 2/1993 |
| JP | 06343644 | 12/1994 |
| JP | H06343644 A | 12/1994 |
| JP | 07265328 | 10/1995 |
| JP | H07265328 A | 10/1995 |
| JP | 08056955 | 3/1996 |
| JP | 08252263 A | 10/1996 |
| JP | 09000492 A | 1/1997 |
| JP | 09010223 | 1/1997 |
| JP | H0910223 A | 1/1997 |
| JP | 11244298 | 9/1999 |
| JP | H11244298 A | 9/1999 |
| JP | 2000342599 A | 12/2000 |
| JP | 2000350732 A | 12/2000 |
| JP | 2001008944 | 1/2001 |
| JP | 2001029356 | 2/2001 |
| JP | 2001128990 A | 5/2001 |
| JP | 2001231870 A | 8/2001 |
| JP | 2002541884 A | 12/2002 |
| JP | 2008142467 A | 6/2008 |
| JP | 2011067633 A | 4/2011 |
| SU | 166452 | 11/1964 |
| SU | 401367 A1 | 10/1973 |
| SU | 727201 A2 | 4/1980 |
| WO | 0164122 A1 | 9/2001 |
| WO | 2004032777 A1 | 4/2004 |
| WO | 2007076924 A2 | 7/2007 |
| WO | 2008043999 A2 | 4/2008 |
| WO | 2008044000 A1 | 4/2008 |
| WO | 20080044000 A1 | 4/2008 |
| WO | 2009094422 A1 | 7/2009 |
| WO | 2010035831 A1 | 4/2010 |
| WO | 2011017168 A2 | 2/2011 |

OTHER PUBLICATIONS

International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
European Search Report dated Nov. 20, 2014, corresponding to European Application No. 14174079.5; 6 pages.
Chinese Notification of the First Office Action with Search (with English Translation), dated Feb. 16, 2015, corresponding to Chinese Patent Application No. 20121057143.4; 19 total pages.

Japanese Office Action (With English Translation), dated Nov. 17, 2015, corresponding to Japanese Application No. 2012-087291; 8 total pages.
Japanese Office Action (with English translation), dated Jan. 12, 2016, corresponding to Japanese Application No. 2010-181337; 6 total pages.
Australian Patent Examination Report 1, dated Aug. 5, 2016, corresponding to Australian Application No. 2015201912; 3 pages.
US. Appl. No. 08/136,098, filed Oct. 14, 1993, Roger A. Stern.
Joseph G. Andriole, M.D., et al., "Biopsy Needle Characteristics Assessed in the Laboratory", Radiology 148: 659-662, Sep. 1983.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May-Jun. 1982.
Medtrex Brochure "The O.R. Pro 300" 1 page; Sep. 1998.
Ni Wei et al., "A Signal Processing Method for the Coriolis Mass Flowmeter Based on a Normalized . . . " Journal of Applied Sciences.cndot. Yingyong Kexue Xuebao, Shangha CN, vol. 23, No. 2:(Mar. 2005); pp. 160-184.
Ogden, "Goertzel Alternative to the Fourier Transform": Jun. 1993 pp. 485-487 Electronics World; Reed Business Publishing, Sutton, Surrey, BG, vol. 99, No. 9, 1687.
Paul G. Horgan, "A Novel Technique for Parenchymal Division During Hepatectomy" The American Journal of Surgery, vol. 181, No. 3, Apr. 2001 pp. 236-237.
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure. "Reducing Needlestick Injuries in the Operating Room" 1 page, Mar. 2001.
Valleylab Brochure, "Valleylab Electroshield Monitoring System" 2 pages, Nov. 1995.
Canadian Office Action dated Mar. 6, 2018 issued in corresponding Canadian Appln. No. 2,773,417.
European Office Action dated Feb. 27, 2018 issued in corresponding EP Appln. No. 14174079.5.
International Search Report PCDUS08/052460 dated Apr. 24, 2008.
Anonymous. (1987) Homer Mammalok. TM. Breast Lesion Needle/Wire Localizer, Namic.RTM. Angiographic Systems Division, Glens Falls, New York, (Hospital products price list), 4 pages.
Anonymous. Blunt Tubes with Finished Ends. Pointed Cannula, Popper & Sons Biomedical Instrument Division. (Products Price List), one page, Jul. 19, 2000.
Anonymous. Ground Cannulae, ISPG, New Milford, CT, (Advertisement) one page, Jul. 19, 2000.
Geddes et al.. "The Measurement of Physiologic Events by Electrical Impedence" Am. J. MI, Jan. Mar. 1964, pp. 16-27.
Ian D. McRury et al., The Effect of Ablation Sequence and Duration on Lesion Shape Using Rapidly Pulsed Radiofrequency Energy Through Electrodes, Feb. 2000, Springer Netherlands. vol. 4; No. 1. pp. 307-320.
Johnson et al. "Evaluation of a Bipolar Electrothermal Vessel Sealing Device in Hemorrhoidectomy" Sales/Product Literature; Jan. 2004.
Johnson, "Use of the LigaSure.TM. Vessel Sealing System in Bloodless Hemorrhoidectomy" Innovations That Work, Mar. 2000.
Joseph Ortenberg, "LigaSure.TM. System Used in Laparoscopic 1st and 2nd Stage Orchiopexy" Innovations That Work, Nov. 2002.
K. Ogata, Modem Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.

(56) References Cited

OTHER PUBLICATIONS

LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences—Yingyong Kexue Xuebao, Shangha CN, vol. 23, No. 2:(Mar. 2005); pp. 160-184.
Olsson M.D. et al., "Radical Cystectomy in Females" Current Surgical Techniques in Urology, vol. 14, Issue 3, 2001.
Organ, L W, "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Peterson et al., "Comparison of Healing Process Following Ligation with Sutures and Bipolar Vessel Sealing" Surgical Technology International (2001).
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Laborite et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
Urologix, Inc.-Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169 (3):845-847.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
European Search Report for European Application No. 12002535.8 dated Aug. 3, 2012.
U.S. Appl. No. 08/483,742, filed Jun. 7, 1995, Roger A. Stern.
U.S. Appl. No. 12/619,323, filed Nov. 16, 2009, Arnold V. DeCarlo.
U.S. Appl. No. 12/619,462, filed Nov. 16, 2009, Casey M. Ladtkow.
U.S. Appl. No. 12/620,289, filed Nov. 17, 2009, Joseph D. Brannan.
U.S. Appl. No. 12/642,623, filed Dec. 18, 2009, Prakash Manley.
U.S. Appl. No. 12/686,726, filed Jan. 13, 2010, Joseph D. Brannan.
U.S. Appl. No. 12/692,856, filed Jan. 25, 2010, Joseph D. Brannan.
U.S. Appl. No. 12/696,671, filed Jan. 29, 2010, Steven Kim.
U.S. Appl. No. 12/696,966, filed Jan. 29, 2010, Steven Kim.
U.S. Appl. No. 12/701,030, filed Feb. 5, 2010, Francesca Rossetto.
U.S. Appl. No. 12/708,974, filed Feb. 19, 2010, Joseph D. Brannan.
U.S. Appl. No. 12/709,014, filed Feb. 19, 2010, Joseph D. Brannan.
U.S. Appl. No. 12/712,864, filed Feb. 25, 2010, Joseph D. Brannan.
U.S. Appl. No. 12/713,429, filed Feb. 26, 2010, Anthony C. Lee.
U.S. Appl. No. 12/713,515, filed Feb. 26, 2010, Anthony C. Lee.
U.S. Appl. No. 12/713,641, filed Feb. 26, 2010, Anthony C. Lee.
U.S. Appl. No. 12/719,657, filed Mar. 8, 2010, Mani N. Prakash.
U.S. Appl. No. 12/722,034, filed Mar. 11, 2010, Casey M. Ladtkow.
U.S. Appl. No. 12/731,367, filed Mar. 25, 2010, Joseph D. Brannan.
U.S. Appl. No. 12/732,508, filed Mar. 26, 2010, Steven Kim.
U.S. Appl. No. 12/732,521, filed Mar. 26, 2010, Steven Kim.
U.S. Appl. No. 12/772,675, filed May 3, 2010, Brian Shiu.
U.S. Appl. No. 12/777,984, filed May 11, 2010, Joseph D. Brannan.
U.S. Appl. No. 12/786,671, filed May 25, 2010, Richard A. Willyard.
U.S. Appl. No. 12/787,639, filed May 26, 2010, Mani N. Prakash.
U.S. Appl. No. 12/792,904, filed Jun. 3, 2010, Ronald J. Podhajsky.
U.S. Appl. No. 12/792,932, filed Jun. 3, 2010, Ronald J. Podhajsky.
U.S. Appl. No. 12/792,947, filed Jun. 3, 2010, Ronald J. Podhajsky.
U.S. Appl. No. 12/792,970, filed Jun. 3, 2010, Ronald J. Podhajsky.
U.S. Appl. No. 12/793,037, filed Jun. 3, 2010, Ronald J. Podhajsky.
U.S. Appl. No. 12/823,211, filed Jun. 25, 2010, Mani N. Prakash.
U.S. Appl. No. 12/826,897, filed Jun. 30, 2010, Brian Shiu.
U.S. Appl. No. 12/826,902, filed Jun. 30, 2010, Brian Shiu.
U.S. Appl. No. 12/837,820, filed Jul. 16, 2010, Joseph D. Brannan.
U.S. Appl. No. 12/839,023, filed Jul. 19, 2010, Ronald J. Podhajsky.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.

(56) References Cited

OTHER PUBLICATIONS

U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/098,199, filed Apr. 29, 2001, Roop L. Mahajan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyms PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure. TM. Vessel Sealing System: A Case Report" Innovations That Work, Feb. 2002.
Humphries Jr. et al., "Finite.cndot.Element Codes to Model Electrical Heating and Nonlinear Thermal Transport in Biological Media", Proc. ASME HTD-355, 131 (1997).
Jarrett et al., "Use of the LigaSure.TM. Vessel Sealing System for Peri-Hilar Vessels in Laparoscopic Nephrectomy" Sales/Product Literature 2000.
Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.

(56) References Cited

OTHER PUBLICATIONS

European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.

(56) References Cited

OTHER PUBLICATIONS

European Search Report EP 10014042.5 extended dated Feb. 18, 2011.
European Search Report EP 10158944.8 extended dated Jun. 21, 2010.
European Search Report EP 10161722.3 extended dated Jun. 16, 2010.
European Search Report EP 10163235.4 dated Aug. 10, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.

\* cited by examiner

MICROWAVE TISSUE DISSECTION AND COAGULATION

CROSS-REFERENCE TO RELATED APPLICATIONS

This application is a divisional application of U.S. patent application Ser. No. 14/922,811, filed Oct. 26, 2015, now U.S. Pat. No. 10,098,697 which is a continuation application of U.S. patent application Ser. No. 13/083,256, now U.S. Pat. No. 9,198,724, filed on Apr. 8, 2011, the entire disclosures of all of which are incorporated by reference herein.

BACKGROUND

1. Technical Field

The present disclosure relates to systems and methods for providing energy to biologic tissue and, more particularly, to an electrosurgical instrument adapted to perform targeted tissue coagulation concurrently with a dissection procedure.

2. Background of Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high radio frequency electrical current to a surgical site to cut, ablate, coagulate or seal tissue. In tissue ablation electrosurgery, the radio frequency energy may be delivered to targeted tissue by an antenna or probe.

There are several types of microwave antenna assemblies in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors, which are linearly aligned and positioned end-to-end relative to one another with an electrical insulator placed therebetween. Helical antenna assemblies include a helically-shaped conductor connected to a ground plane. Helical antenna assemblies can operate in a number of modes including normal mode (broadside), in which the field radiated by the helix is maximum in a perpendicular plane to the helix axis, and axial mode (end fire), in which maximum radiation is along the helix axis. The tuning of a helical antenna assembly may be determined, at least in part, by the physical characteristics of the helical antenna element, e.g., the helix diameter, the pitch or distance between coils of the helix, and the position of the helix in relation to the probe assembly to which it is mounted.

The typical microwave antenna has a long, thin inner conductor that extends along the longitudinal axis of the probe and is surrounded by a dielectric material and is further surrounded by an outer conductor around the dielectric material such that the outer conductor also extends along the axis of the probe. In another variation of the probe that provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or combinations thereof. In the case of tissue ablation, a high radio frequency electrical current in the range of about 300 MHz to about 10 GHz is applied to a targeted tissue site to create an ablation volume, which may have a particular size and shape. Ablation volume is correlated to antenna design, antenna tuning, antenna impedance and tissue impedance.

Certain surgical procedures require use of a cutting instrument, e.g., a scalpel or shears, to resect tumors and/or other necrotic lesions, which may necessitate severing one or more blood vessels and thus cause undesirable bleeding. Such bleeding may, in turn, obscure a surgeon's view of the surgical site and generally require the surgeon to attend to controlling the bleeding, rather than to the primary surgical objective. This, in turn, may lead to increased operative times and suboptimal surgical outcomes.

SUMMARY

The present disclosure is directed to a surgical instrument utilizing microwave energy for simultaneous coagulation and dissection of tissue. In an embodiment, the instrument is a handheld surgical device having a curvate elongated shaft. The distal end of the shaft includes a directional microwave radiating assembly having a blade adapted to dissect tissue. The proximal end of the shaft may include a handle and one or more actuators, e.g., a pushbutton adapted to activate the delivery of coagulation energy. Ablation energy is provided to the microwave aperture by a coaxial feed line disposed within the shaft.

The microwave aperture may have a hemispherical shape, an elongated cup shape, a clamshell shape, a cylindrical shape, a rounded cylindrical shape, a parabolic shape, and/or various combinations thereof. The aperture includes metallic shielding on all but a bottom surface, which remains unshielded to enable the targeted delivery of microwave coagulation energy to tissue. The use of a blade, together with the concurrent application of coagulation energy enables a surgeon to perform dissection using the blade, while simultaneously performing coagulation on the tissue, to control or eliminate bleeding at the operative site. Used in this manner, a surgical instrument in accordance with an embodiment of the present disclosure may enable a physician to simultaneously and rapidly coagulate and dissect highly perfused solid organs, e.g., the liver, which, in turn, may reduce operative times, decrease risk factors, shorten recovery times, and improve patient outcomes.

In an embodiment, the surgical instrument comprises a handle and a shaft extending distally from the handle. The shaft includes an outer hypotube, a lumen coaxially disposed within the hypotube and extending beyond a distal end thereof, a coaxial feedline coaxially disposed within the lumen, and having an inner conductor and an outer conductor disposed coaxially about the inner conductor, and a coolant tube coaxially disposed between the lumen and the coaxial feedline to form an inflow conduit and an outflow conduit. The instrument further includes a dissecting head assembly coupled to a distal end of the shaft. The dissecting head assembly includes a dielectric core having a substantially planar radiating surface and at least one non-radiating surface, a reflective coating disposed on the at least one non-radiating surface of the dielectric core, and a blade extending from the radiating surface.

The present disclosure is also directed to a surgical dissection and coagulation system. In an embodiment, the surgical dissection and coagulation system comprises a source of microwave coagulation energy and a surgical instrument as described hereinabove that is adapted to operably couple to the source of microwave coagulation energy. The disclosed surgical dissection and coagulation system may include a source of coolant and wherein the surgical instrument is adapted to operably couple to the source of coolant.

Also disclosed is a method for concurrently performing dissection and coagulation. The method comprises positioning a dissection head of a surgical instrument over tissue, wherein the dissection head includes a tissue-contacting surface configured to apply coagulation energy to tissue, and a blade protruding from the tissue-contacting surface. The tissue-contacting surface is brought into contact with targeted tissue to begin an incision and coagulation energy is applied to the targeted tissue, and the dissection head is drawn across the targeted tissue to continue the incision.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
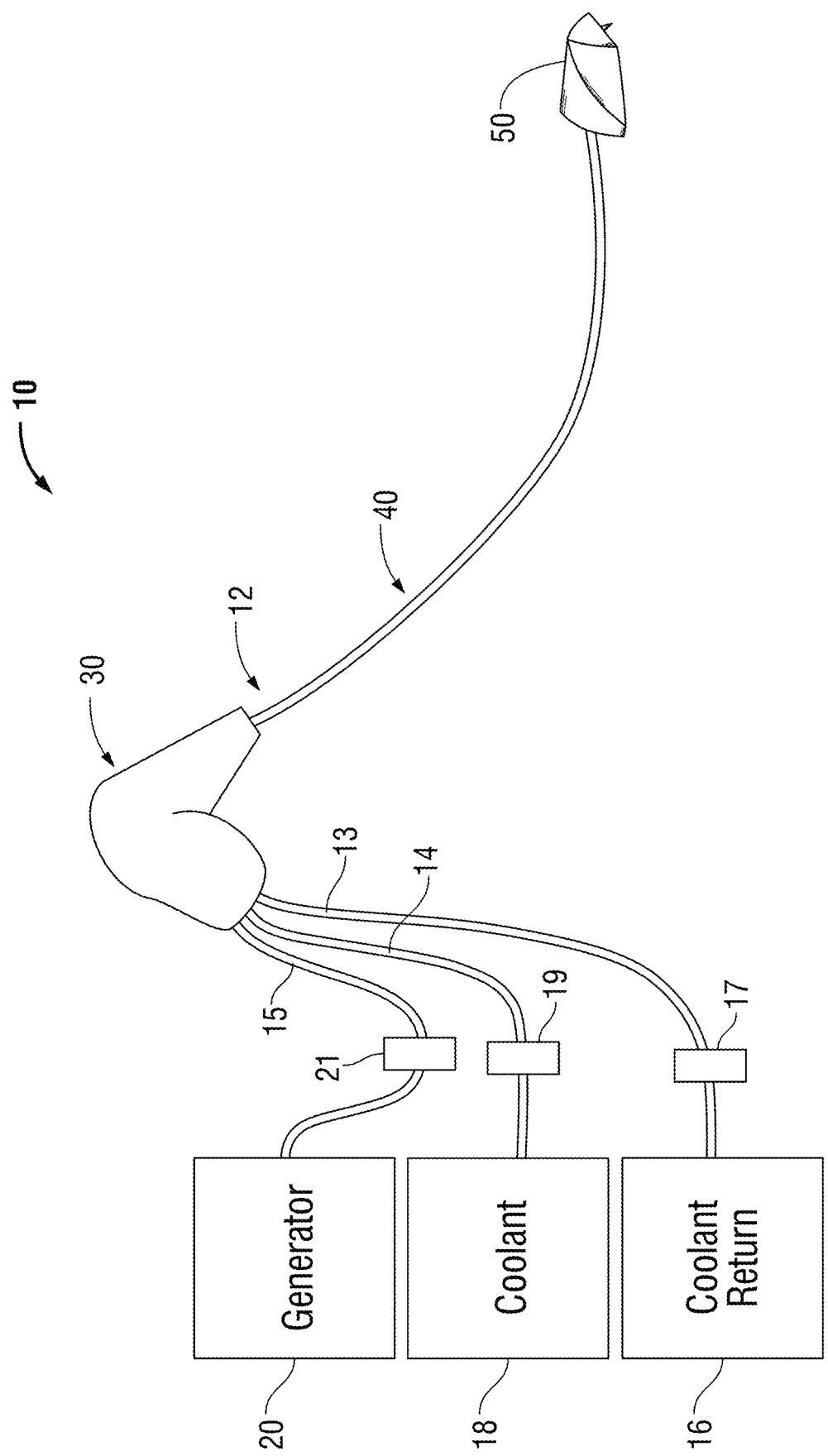
FIG. 1 shows a diagram of an embodiment of a coagulation and dissection system in accordance with an embodiment of the present disclosure.

Particular embodiments of the present disclosure are described hereinbelow with reference to the accompanying drawings; however, the disclosed embodiments are merely examples of the disclosure, which may be embodied in various forms. Well-known functions or constructions and repetitive matter are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. In this description, as well as in the drawings, like-referenced numbers represent elements which may perform the same, similar, or equivalent functions.

In the drawings and in the descriptions that follow, the term "proximal," as is traditional, shall refer to the end of the instrument that is closer to the user, while the term "distal" shall refer to the end that is farther from the user. In addition, as used herein, terms referencing orientation, e.g., "top", "bottom", "up", "down", "left", "right", "clockwise", "counterclockwise", and the like, are used for illustrative purposes with reference to the figures and features shown therein. Embodiments in accordance with the present disclosure may be practiced in any orientation without limitation.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as microwave ablation, radio frequency (RF) ablation, or microwave ablation assisted resection. As it is used in this description, "transmission line" generally refers to any transmission medium that can be used for the propagation of signals from one point to another.

Various embodiments of the present disclosure provide electrosurgical devices operably associated with directional reflector assemblies for treating tissue and methods of directing electromagnetic radiation to a target volume of tissue. Embodiments may be implemented using electromagnetic radiation at microwave frequencies, or, at other frequencies. An electrosurgical system having an aperture assembly that includes an energy applicator operably associated with a directional reflector assembly, according to various embodiments, is configured to operate between about 300 MHz and about 10 GHz with a directional radiation pattern.

Various embodiments of the presently disclosed electrosurgical devices, directional reflector assemblies, thereto and electrosurgical system including the same are suitable for microwave ablation and for use to pre-coagulate tissue for microwave ablation-assisted surgical resection. Although various methods described hereinbelow are targeted toward microwave ablation and the destruction and/or resection of targeted tissue, methods for directing electromagnetic radiation may be used with other therapies in which the target tissue is partially destroyed, damaged, or dissected, such as, for example, to prevent the conduction of electrical impulses within heart tissue. In addition, the teachings of the present disclosure may apply to a dipole, monopole, helical, or other suitable type of microwave antenna.

FIG. 1 shows a microwave dissection and coagulation system 10 in accordance with an embodiment of the present disclosure. The dissection and coagulation system 10 includes an ablation instrument 12 that is operably connected by a coaxial cable 15 to connector 21, which further operably connects instrument 12 to a generator assembly 20. Instrument 12 is operably coupled to a coolant source 18, e.g., saline or deionized water, by a coolant supply tube 14 that is coupled to the coolant source 18 by a fluid coupler 19. Coolant exits instrument 12 via coolant drain tube 13 that is coupled to a coolant return vessel 16 by fluid coupler 17. Fluid couplers 17 and 19 may include any suitable fluid coupling device, including without limitation a luer-lock coupling. Used coolant may be recirculated from coolant return 16 to coolant supply 18 for subsequent re-use (e.g., after being cooled by a heat exchanger, radiator, refrigerant-based device, peltier module, and the like) or may simply be discarded after use. Fluid flow rate may also be monitored by a flow rate sensor (not explicitly shown).

Generator assembly 20 may be a source of ablation energy, e.g., microwave or RF energy in the range of about 915 MHz to about 25.0 GHz. In various embodiments, generator 20 operates at 915 MHz, 2450 MHz, and/or 5800 Mhz. Instrument 12 is adapted for use in various surgical procedures, and in particular, for use in dissection and coagulation procedures. Instrument 12 includes a handle assembly 30 coupled to a proximal end of a shaft 40, and a dissection head 50 coupled to a distal end of the shaft 40. Dissection head 50 is configured to enable the simultaneous dissection and coagulation of tissue, as described in further detail below. Instrument 12 may be used in minimally-invasive (e.g., laparoscopic) or open surgical procedures.

Figure 2:
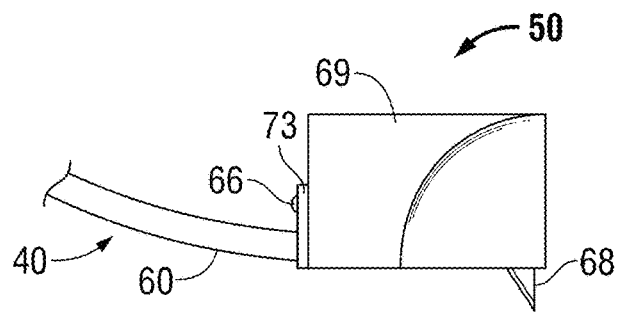
FIG. 2 shows a side view of an embodiment of a dissector head in accordance with an embodiment of the present disclosure.
Figure 3:
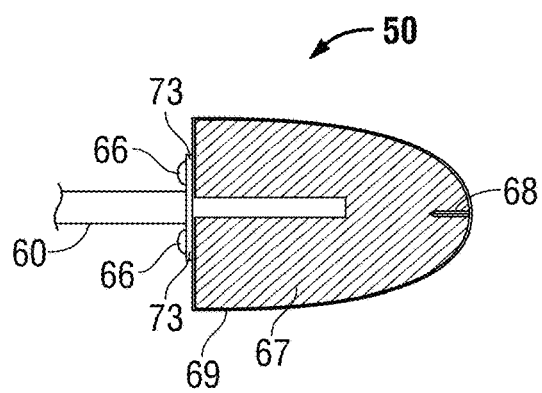
FIG. 3 shows a bottom view of an embodiment of a dissector head in accordance with an embodiment of the present disclosure.
Figure 4:
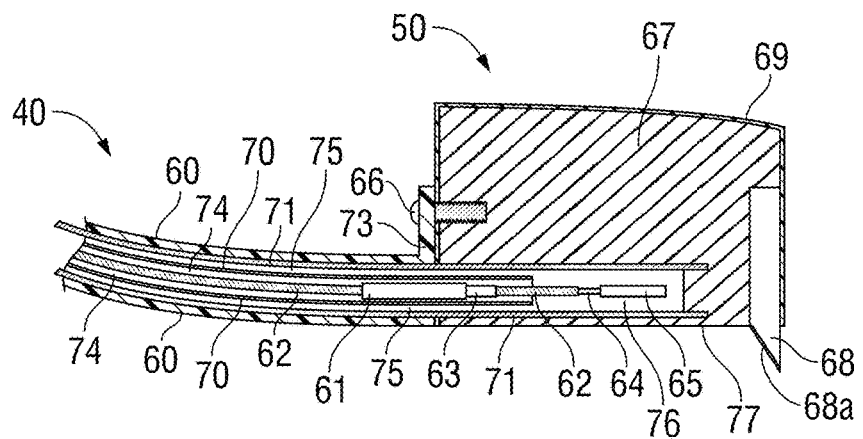
FIG. 4 shows a side, cutaway view of an embodiment of a dissector head in accordance with an embodiment of the present disclosure.

FIGS. 2-4 further illustrate details of an embodiment of shaft 40 and dissection head 50 in accordance with the present disclosure. Shaft 40 includes an outer hypotube 60 that is formed from a substantially rigid, heat-resistant material. In some embodiments, hypotube 60 may be formed from stainless steel. In the illustrated embodiment, shaft 40 has a generally curvate contour that places handle 30 and dissection head 50 in an ergonomically-advantageous orientation that facilitates the use thereof in surgical procedures. A mounting flange 73 is coupled to a distal end of hypotube 60 and is adapted to couple hypotube 60 to dissection head 50. In some embodiments, flange 73 is secured to dissection head 50 by fasteners 66, which may be threaded fasteners (e.g., screws). Flange 73 may be fixed to hypotube by any suitable manner, including without limitation brazing, welding, threaded fastening, or flange 73 and hypotube 60 may be integrally formed. In another envisioned embodiment, hypotube 60 may be coupled to dissection head 50 by any suitable manner including adhesive, overmolding, or integral formation.

Shaft 40 includes a number of elements arranged concentrically therein that are adapted to deliver electrosurgical energy and coolant to dissection head 50, and to remove coolant from dissection head 50. Electrosurgical (e.g., microwave) energy is delivered by a coaxial feedline 55, coolant is delivered via a fluid inflow conduit 74, and coolant is removed via a fluid outflow conduit 75, as described in detail below.

A lumen 71 is disposed within hypotube 60 and extends beyond a distal end of hypotube 60 into a dielectric region 67 of dissection head 50. Lumen 71 may be formed from a thermosetting polymer such as, without limitation, polyimide. Shaft 40 includes coaxial feedline 55 disposed along a longitudinal axis thereof. Coaxial feedline 55 includes an inner conductor 78 coaxially disposed within an outer conductor 62 having an insulator 64 disposed therebetween. A coolant tube 70 is concentrically disposed between lumen 71 and feedline 55 to divide the volume therebetween into fluid inflow conduit 74 and fluid outflow conduit 75. At their respective distal ends, inflow conduit 74 and outflow conduit 75 are in fluid communication with a cooling chamber 76 defined within a distal region of lumen 71 within dissection head 50. During use, coolant circulates distally through inflow conduit 74, flows into coolant chamber 76, and evacuates proximally through outflow conduit 75.

A balun dielectric 63 is concentrically disposed about feedline 55. In an embodiment, balun dielectric 63 is positioned within lumen 71 at or near a juncture of a distal end of hypotube 60 and a proximal side of dissection head 50. Balun dielectric 63 may be formed from any suitable heat-resistant material having a low electrical conductivity, for example without limitation, polytetrafluoroethylene (a.k.a. PTFE or Teflon®, manufactured by the E.I. du Pont de Nemours and Co. of Wilmington, Del., USA). A balun outer conductor 61 is concentrically disposed about balun dielectric 63. In some embodiments, a distal portion 56 of balun dielectric 63 extends distally beyond a distal end of balun outer conductor 61. Balun outer conductor 61 may be formed from any suitable electrically conductive material, e.g., rolled copper foil, copper tubing, and the like. In some embodiments, balun outer conductor 61 may be formed from Polyflon™ electroplated PTFE distributed by the Polyflon Company of Norwalk, Conn., USA. Balun dielectric 63 and balun outer conductor 61 are arranged to form a quarter-wave short-circuiting balun to contain the radiated microwave energy to the region under the tissue-contacting radiating surface 77 of dissection head 50 and/or within the reflective outer layer 69 of dissection head 50. Near a distal end of coaxial feedline 55, the inner conductor 78 and insulator 64 extend beyond the outer conductor 62. The inner conductor 78 extends beyond a distal end of insulator 64 and is operably coupled to a distal radiating section 65. An exposed section 57 of insulator 64 situated immediately proximally of distal radiating section 65 acts as a feed point and/or a feed gap thereto.

As shown in FIGS. 2, 3, and 4, dissection head 50 includes a solid core dielectric region 67 having a reflective outer layer 69 disposed on the upper portion thereof, e.g., top and all sides thereof. Dielectric region 67 includes a generally planar, exposed, bottom radiating surface 77. Dielectric region 67 may be formed from any suitable dielectric material having low-loss dielectric loading properties that possesses sufficient mechanical and biocompatible properties to withstand conditions associated with surgical procedures, including without limitation ceramic material; PTFE; Teflon®; or Ultem™ amorphous thermoplastic polyetherimide (PEI) resin distributed by SABIC Innovative Plastics of Pittsfield, Mass., USA. Reflective outer layer 69 may be formed from any suitable material having the capability to reflect microwave energy, such as without limitation copper plating, copper foil, or Polyflon™ electroplated PTFE.

As shown, dissection head 50 has a generally wedge-like shape; however, it is envisioned the dissection head may have any suitable shape or section thereof that facilitates dissection and coagulation, including without limitation, a generally hemispherical shape, a generally elongated hemispherical shape, a generally clamshell shape, a generally parabolic shape, a generally cylindrical shape, a generally semicylindrical shape, a generally conical shape, a generally discoid shape, and a generally frustoconical shape.

Dissection head 50 also includes a blade 68 extending downward from bottom radiating surface 77 and oriented in substantial alignment with a longitudinal axis of the instrument 12. As shown, blade 68 has a cutting edge 68a configured to cut tissue when instrument 12 is drawn in a proximal direction; however, it is envisioned blade 68 and/or cutting edge 68a may be oriented in other directions, e.g., arranged to cut tissue when the instrument 12 is drawn distally, laterally (left or right), or any angle therebetween. In some embodiments, the blade 68 is movable. For example, and without limitation, blade 68 may be rotatable about a vertical axis thereof and/or blade 68 may be retractable.

Dissection head 50 may include a lubricious coating (not explicitly shown) on portions of reflective outer layer 69 and/or bottom radiating surface 77, that may be formed from any suitable lubricious material that is heat-resistant and biocompatible and that reduces the possibility of tissue and other biomaterials from adhering to dissection head 50, such as, without limitation, polytetrafluoroethylene, polyethylene tephthalate, and parylene coating.

Figure 5:
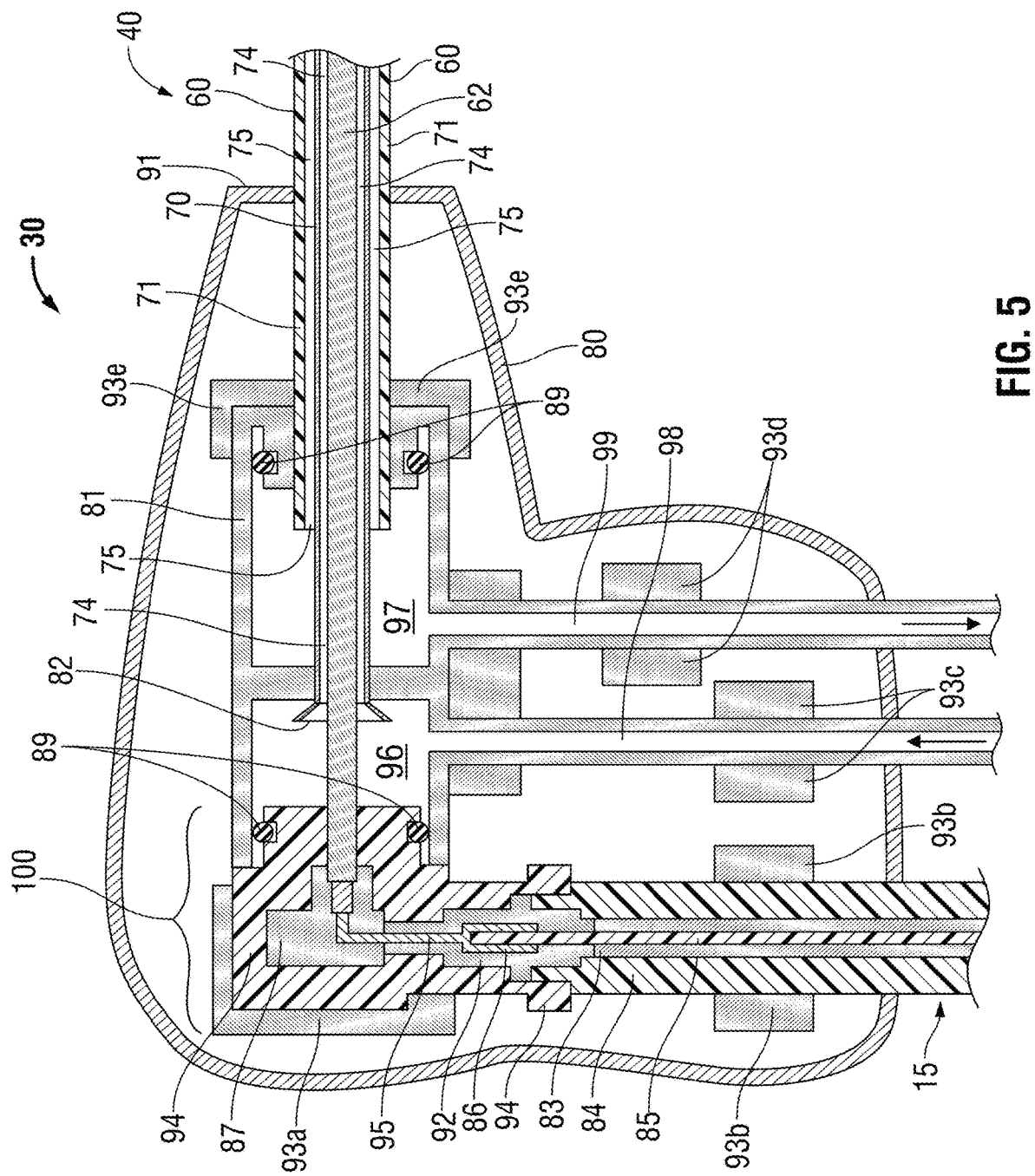
FIG. 5 shows a side, cutaway view of an embodiment of a handle assembly in accordance with an embodiment of the present disclosure.

Turning now to FIG. 5, handle assembly 30 includes a housing 80 that may be assembled from a two piece (left and right half) clamshell-type assembly that is joined along a common edge by any suitable manner of attachment, e.g., welding (laser, sonic, chemical, etc.), adhesive, mechanical fasteners, clips, threaded fasteners and the like. A proximal end of shaft 40 and associated internal components therein extend into a distal end 91 of housing 80 to couple shaft 40 to housing 80 and to facilitate the electrical and fluidic coupling of shaft 40 and dissection head 50 to generator 20, coolant supply 18, and coolant return 16.

A coolant manifold 81 is disposed within housing 80, the coolant manifold 81 having an inflow plenum 96 that is in fluid communication with inflow conduit 74, and an outflow plenum 97 that is in fluid communication with outflow conduit 75. Inflow port 98 is in fluid communication with inflow plenum 96 to facilitate circulation of coolant from coolant source 18 though instrument 12. Similarly, outflow port 99 is in fluid communication with outflow plenum 97 to facilitate the expulsion of coolant from instrument 12. A proximal end of lumen 70 may include a flare 82 to enhance the flow of coolant into inflow conduit 74.

Housing 80 includes a 90° coaxial coupler assembly 100 configured operably receive and electrically couple coaxial cable 15 to coaxial feedline 55. Coupler assembly 100 includes an outer conductor transition 94 that is configured to engage outer conductor 84 of coaxial cable 15, and an inner conductor transition 95 that is configured to engage inner conductor 85 of coaxial cable 15. Inner conductor transition 95 may include a female receptacle 86 that is dimensioned to receive inner conductor 85 of coaxial cable 15. Insulating regions 87 and 92 provide electrical isolation between outer conductor transition 94 and inner conductor transition 95, and may be formed from airspace or solid dielectric material, such as ceramic or polymeric material. When insulating regions 87 and 92 are formed from solid dielectric material, insulating regions 87 and 92 may provide physical support for outer conductor transition 94 and inner conductor transition 95.

As shown in FIG. 5, a pair of elastomeric o-rings 89 provide a fluidic seal between coupler assembly 100 and inflow plenum 96, and between shaft 40 and outflow plenum 97. In some embodiments, coupler assembly 100 and inflow plenum 96, and shaft 40 and outflow plenum 97, may be respectively sealed by an adhesive compound (e.g., silicone or epoxy sealant), compression fitting, threaded fitting, or any other suitable form of fluidic seal. Housing 80 also includes a plurality of mechanical stops 93a-93f that are configured to engage and secure the aforementioned components of handle 30 within housing 80.

Figure 6A:
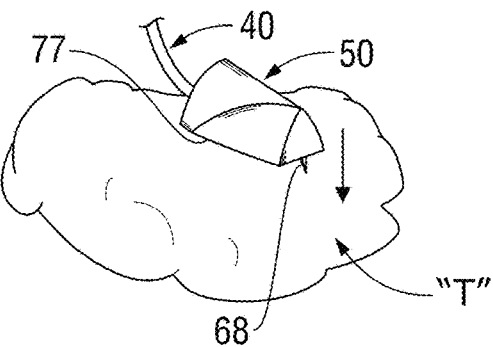
FIGS. 6A-6C show a coagulation and dissection procedure performed utilizing a coagulation and dissection system in accordance with an embodiment of the present disclosure.
Figure 6B:
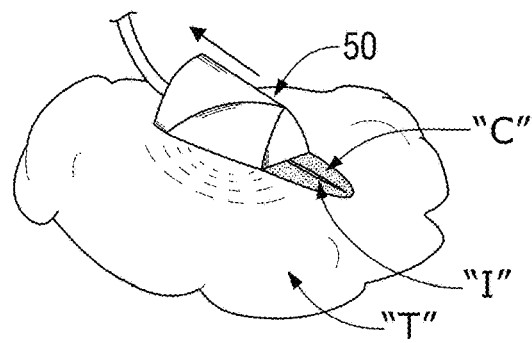
Figure 6C:
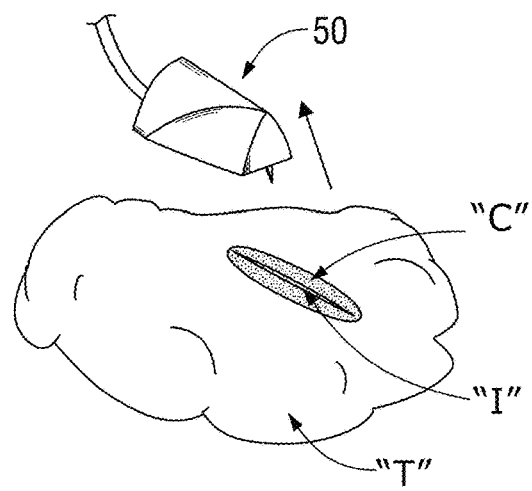

In FIGS. 6A-C a method of performing dissection and coagulating of tissue utilizing a microwave dissection and coagulation system in accordance with an embodiment of the present disclosure is shown. The illustrated example may be performed as an open surgical procedure, or may be performed using minimally-invasive (e.g., laparoscopic) techniques. As seen in FIG. 6A, dissection head 50 of instrument 12 is positioned over targeted tissue "T" such that blade 68 is adjacent to the starting point of the desired incision. Note that a curvate shape of shaft 40 advantageously enables the surgeon's hand (not explicitly shown) to be positioned well above the desired cutting plane while grasping handle 30. The tissue-contacting radiating surface 77 of dissection head 50 is then brought into contact with tissue "T", thereby piercing tissue "T" with blade 68 to begin an incision.

Upon contacting tissue "T" with tissue-contacting radiating surface 77 of dissection head 50, the surgeon activates the generator 20 to commence delivery of coagulation energy to tissue at the operative site. Activation of the generator 20 may also cause coolant to flow through instrument 12 via the inflow and outflow structures described hereinabove. Concurrently with the delivery of coagulation energy to tissue, the surgeon creates an incision "I" by drawing the dissection head 50 in a proximal direction over tissue "T". As the incision is formed, the coagulation energy radiated from dissection head 50 coagulates tissue "T" within a coagulation region generally indicated by reference letter "C".

In one embodiment of the disclosed method, dissection and coagulation is performed by moving the dissection head at a rate of about 3.5 mm/sec, which may provide a coagulation region having a width of about 1 cm and a depth of about 1 cm.

The size (e.g., width and/or depth) of coagulation region "C" may be determined by one or more of a plurality of procedural parameters, either individually or in combination. For example, and without limitation, the size of coagulation region "C" may be determined by the shape of dissection head 50. Instruments may be provided to the surgeon in a variety of shapes and sizes that will enable the surgeon to select the size of desired coagulation region "C" in accordance with surgical objectives. Coagulation size may also be determined by the power level of the delivered coagulation energy, the frequency of the delivered coagulation energy, a modulation of the delivered coagulation energy, and/or the rate at which the surgeon moves the dissection head to create the incision "I".

Once the desired incision "I" has been created, the surgeon deactivates the generator and coolant flow, and withdraws the dissection head 50 form the surgical site as depicted in FIG. 6C.

The described embodiments of the present disclosure are intended to be illustrative rather than restrictive, and are not intended to represent every embodiment of the present disclosure. It is to be understood that the steps of a method provided herein may be performed in combination and/or in a different order than presented herein without departing from the scope and spirit of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. A method for performing dissection and coagulation, comprising:
   positioning a dissection head of a surgical instrument in contact with tissue, wherein the dissection head includes a tissue-contacting surface and a blade;
   transmitting microwave energy to the tissue-contacting surface through a coaxial feedline having an inner conductor and an outer conductor, the inner conductor and the outer conductor being electrically isolated from the blade;
   applying coagulation energy to the tissue through the tissue-contacting surface; and
   moving the dissection head across the tissue thereby forming an incision with the blade.

2. The method in accordance with claim 1, wherein the coagulation energy is deflected toward and out through the tissue-contacting surface of the dissection head by a reflective surface of the dissection head.

3. The method in accordance with claim 2, wherein the reflective surface is disposed on an inner surface that is opposite the tissue-contacting surface.

4. The method in accordance with claim 1, wherein the inner conductor and the outer conductor of the coaxial feedline are disposed within a dielectric core.

5. The method in accordance with claim 1, wherein the blade is oriented substantially perpendicular to the tissue-contacting surface.

6. The method in accordance with claim 1, wherein the blade has a cutting edge oriented in a proximal direction such that the cutting edge cuts tissue when the dissection head is moved in the proximal direction.

7. The method in accordance with claim 1, wherein the blade has a cutting edge oriented in a distal direction such that the cutting edge cuts tissue when the dissection head is moved in the distal direction.

8. The method in accordance with claim 1, wherein the dissection head has a shape selected from the group consisting of a generally wedge-like shape, a generally hemispherical shape, a generally elongated hemispherical shape, a generally clamshell shape, a generally parabolic shape, a generally semicylindrical shape, a generally conical shape, a generally discoid shape, and a generally frustoconical shape.

9. The method in accordance with claim 1, further comprising:
   applying a lubricious coating disposed on the tissue-contacting surface.

10. The method in accordance with claim 1, further comprising:
   coupling a proximal portion of the coaxial feedline to a source of microwave energy.

11. The method in accordance with claim 1, wherein the tissue-contacting surface of the dissection head is planar.

* * * * *